United States Patent
Jhon et al.

(10) Patent No.: US 10,401,320 B2
(45) Date of Patent: Sep. 3, 2019

(54) METHOD OF FABRICATING 3-DIMENSIONAL TRANSISTOR SENSOR, THE SENSOR AND SENSOR ARRAY THEREOF

(71) Applicant: KOREA INSTITUTE OF SCIENCE AND TECHNOLOGY, Seoul (KR)

(72) Inventors: Young In Jhon, Seoul (KR); Young Tae Byun, Seoul (KR); Yong Tae Kim, Seoul (KR); Young Min Jhon, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/939,721

(22) Filed: Mar. 29, 2018

(65) Prior Publication Data
US 2019/0072516 A1    Mar. 7, 2019

(30) Foreign Application Priority Data
Sep. 5, 2017 (KR) .................. 10-2017-0113361

(51) Int. Cl.
*G01N 27/414* (2006.01)
*H01L 29/66* (2006.01)
(Continued)

(52) U.S. Cl.
CPC ....... *G01N 27/4146* (2013.01); *G01N 27/414* (2013.01); *G01N 27/4145* (2013.01);
(Continued)

(58) Field of Classification Search
CPC ............ G01N 27/4146; G01N 27/4145; H01L 27/0886; H01L 21/823462; H01L 29/66795; H01L 29/785
See application file for complete search history.

(56) References Cited

U.S. PATENT DOCUMENTS

2011/0033952 A1    2/2011   Khater et al.
2013/0291627 A1*  11/2013   Hu .................... G01N 27/4146
                                                        73/61.61
(Continued)

FOREIGN PATENT DOCUMENTS

KR    10-2017-0028820 A    3/2001

OTHER PUBLICATIONS

Korean Office Action dated Oct. 21, 2018.

*Primary Examiner* — Karen Kusumakar
(74) *Attorney, Agent, or Firm* — Rabin & Berdo, P.C.

(57) ABSTRACT

Provided are a method of fabricating a 3-dimensional transistor sensor and the sensor and a sensor array thereof. The method of fabricating the 3-dimensional transistor sensor includes forming an insulating layer on a silicon substrate, forming a silicon layer on the insulating layer and forming a 3-dimensional silicon fin by etching the silicon layer, forming a source area and a source electrode at one end of the silicon fin, forming a drain area and a drain electrode at the other end the silicon fin, and forming a gate area at a center of the silicon fin, surrounding three surfaces of a gate with a gate insulating layer, forming a sensing gate layer configured to surround a portion of the gate insulating layer, and sealing an upper portion of the gate insulating layer excluding the sensing gate layer.

13 Claims, 11 Drawing Sheets

(51) Int. Cl.
*H01L 21/8234* (2006.01)
*H01L 29/78* (2006.01)
*H01L 27/088* (2006.01)
*H01L 27/12* (2006.01)

(52) U.S. Cl.
CPC .. *H01L 21/823462* (2013.01); *H01L 27/0886* (2013.01); *H01L 27/1203* (2013.01); *H01L 29/66795* (2013.01); *H01L 29/785* (2013.01)

(56) References Cited

U.S. PATENT DOCUMENTS

2015/0053925 A1* 2/2015 Liu .................... G01N 27/4145
257/24
2018/0175184 A1* 6/2018 Then ...................... H01L 29/78

* cited by examiner

METHOD OF FABRICATING 3-DIMENSIONAL TRANSISTOR SENSOR, THE SENSOR AND SENSOR ARRAY THEREOF

CROSS-REFERENCE TO RELATED APPLICATION

This application claims priority to and the benefit of Korean Patent Application No. 2017-0113361, filed on Sep. 5, 2017, the disclosure of which is incorporated herein by reference in its entirety.

BACKGROUND

1. Field of the Invention

The present invention relates to a transistor sensor, and more particularly, to a new type of 3-dimensional transistor sensor and a method of fabricating the same.

2. Discussion of Related Art

Recently, the Internet of things (IoT) has entered the spotlight. The IoT is an intelligent technology and service which enables objects to connect based on the Internet and to communicate information between people and objects and between objects. In the IoT, sensors for recognizing a surrounding environment are required. Sensors used in the IoT should be able to sense various materials at a very high speed while minimizing operation power consumption to be suitable for a mobile environment. Until now, a transistor element has been mainly used as a basic element structure of a sensor to achieve the above requirement.

A method of fabricating a field effect transistor (FET) using a silicon on insulator (SOI) substrate has been proposed as a method of increasing a speed while fundamentally lowering an operating voltage to reduce operation power consumption of such a transistor element. The SOI substrate is a substrate on which a silicon oxide layer is formed on a silicon substrate and a silicon layer is bonded to the silicon oxide layer.

A conventional transistor sensor has a planar element structure in which a source, a gate, and a drain are made using a silicon substrate or a thin film. However, due to a structure of a transistor element formed on a surface layer of the silicon substrate, there is a limitation in minimizing power consumption and maximizing sensitivity by an electric field, a leakage current, a parasitic capacitor, current transfer characteristic deterioration, or the like through a bulk substrate existing below a surface of the silicon substrate. In addition, planar use of gates is limited to reduction of element size and improvement of a degree of integration of sensor array through line width reduction, minimization of power consumption, and very high-speed operations. Even when an SOI substrate is used instead of a silicon substrate, a problem still occurring in a silicon bulk substrate according to a thickness of silicon on an oxide layer cannot be fundamentally blocked. Further, a thin-film type silicon substrate has fatal defects in crystallinity and uniformity of a material, and thus it is difficult to achieve reliability, a very high speed, and low power.

In order to address such problems, recently, many studies on a finFET type sensor in which a fin type source-channel-drain silicon by three-dimensionally etching silicon is made and three surfaces of a channel, which are both side surfaces and an upper surface of the channel, are used as gates are underway. However, in order to operate ultra-high sensitive and ultra-low-power sensing, more improved technology is required.

DOCUMENT OF RELATED ART

Patent Document (Patent Document 1) Korean Patent Application Publication No. 10-2017-0028820

SUMMARY OF THE INVENTION

The present invention is directed to a new type of 3-dimensional transistor sensor capable of maximizing sensitivity, minimizing power consumption, and operating at a very high speed, which are difficult to achieve with a conventional transistor sensor.

One aspect of the present invention provides a method of fabricating a 3-dimensional transistor sensor including forming an insulating layer on a silicon substrate, forming a silicon layer on the insulating layer and forming a 3-dimensional silicon fin by etching the silicon layer, forming a source area and a source electrode at one end of the silicon fin, forming a drain area and a drain electrode at the other end the silicon fin, and forming a gate area at a center of the silicon fin, surrounding three surfaces of a gate with a gate insulating layer, forming a sensing gate layer configured to surround a portion of a drain or a source side of the gate insulating layer, and sealing an upper portion of the gate insulating layer excluding the sensing gate layer.

Preferably, the 3-dimensional silicon fin may have a height of 20 nm to 1 μm and a width of 10 nm to 500 nm.

Preferably, a P-type impurity may be implanted into the source area, an N-type impurity may be implanted into the drain area, and an impurity may not be implanted into the gate area.

Preferably, the sensing gate layer may be formed by removing a portion of the gate insulating layer, which is in contact with the drain or the source, or the sensing gate layer may be formed as a sensing gate electrode on a portion of the gate insulating layer.

Preferably, the sensing gate layer material may be made of any one of $SiO_2$, $Si_3N_4$, $Al_2O_3$, $Pr_2O_3$, InN, $RuO_2$, RuN, $Ta_2O_5$, $SnO_2$, $V_2O_5$, $TiO_2$, $WO_3$, ZnO, $Fe_2O_3$, CuO, $Cr_2O_3$, an antibody, an enzyme, a nucleic acid (DNA), a nanomaterial, valinomicine, fluorescein, alizarin complexone, and an organic conducting polymer (OCP).

Preferably, the sensing gate layer has a length of 10 nm to 500 nm.

Another aspect of the present invention provides a 3-dimensional transistor sensor including a transistor having a source-gate-drain on a 3-dimensional silicon fin formed on a silicon on insulator (SOI) substrate, a gate insulating layer configured to surround three surfaces of the gate, and a sensing gate layer configured to surround a portion of the gate insulating layer and formed by removing a portion of the gate insulating layer, which is in contact with the drain or the source, wherein, when a material is sensed by the sensing gate layer, a current flows between the source and the drain.

Still another aspect of the present invention provides a 3-dimensional transistor sensor including a transistor having a source-gate-drain on a 3-dimensional silicon fin formed on an SOI substrate, a gate insulating layer configured to surround three surfaces of the gate, and a sensing gate electrode configured to surround a portion of the gate insulating layer and formed on a portion of the gate insulating layer in contact with the drain or the source, wherein when a material is sensed by the sensing gate electrode, a current flows between the source and the drain.

Preferably, when no voltage is applied to the transistor, an off state in which no current flows between the source and the drain may be maintained, and when a material is sensed by the sensing gate layer or the sensing gate electrode, an electric field through the sensing gate layer or the sensing gate electrode may be formed due to the material.

Preferably, materials for the sensing gate layer or the sensing gate electrode may include any one of $SiO_2$, $Si_3N_4$, $Al_2O_3$, $Pr_2O_3$, InN, $RuO_2$, RuN, $Ta_2O_5$, $SnO_2$, $V_2O_5$, $TiO_2$, $WO_3$, ZnO, $Fe_2O_3$, CuO, $Cr_2O_3$, an antibody, an enzyme, a nucleic acid (DNA), a nanomaterial, valinomicine, fluorescein, alizarin complexone, and an organic conducting polymer (OCP).

Yet another aspect of the present invention provides a 3-dimensional transistor sensor array in which 3-dimensional transistor sensors are arranged in an array form.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
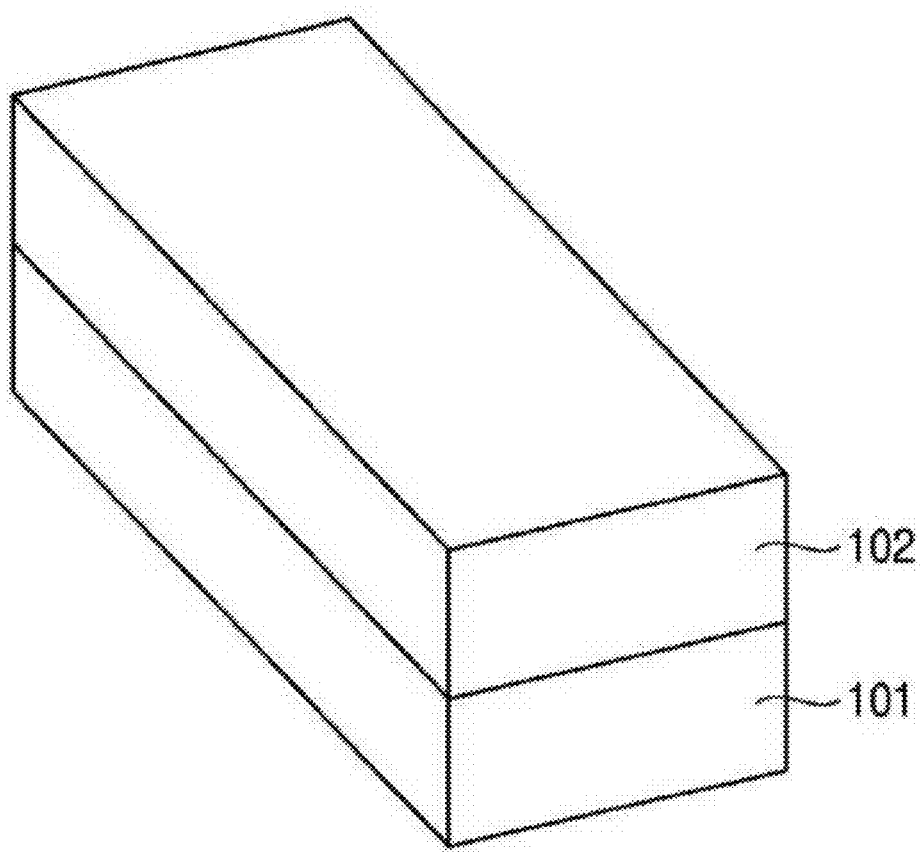
FIGS. 1 to 7 are schematic views for describing a method of fabricating a 3-dimensional transistor sensor according to an exemplary embodiment of the present invention.

Hereinafter, advantages and features of the present invention, and methods of achieving the same will be clearly understood with reference to the accompanying drawings and the following detailed embodiments. However, the present invention is not limited to the embodiments to be disclosed, but may be implemented in various different forms. The embodiments are provided in order to complete the present disclosure and fully explain the scope of the present invention for those skilled in the art to which the present invention belongs. The scope of the present invention is defined by the appended claims. Like reference numerals indicate like components throughout the specification. The term "and/or" includes any and all combinations of one or more referents.

In each step, identification codes (e.g., a, b, c, etc.) are used for convenience of explanation and do not describe the order of the steps, and each step may be performed differently from the stated order unless explicitly stated in the context. That is, the steps may be performed in the same order as described, performed substantially at the same time, or performed in an order opposite to the described order.

The terms used herein are provided to only describe embodiments of the present invention and not for purposes of limitation. Unless the context clearly indicates otherwise, the singular forms include the plural forms. It will be understood that the terms "comprise" or "comprising" when used herein, specify some stated components, steps, operations and/or elements, but do not preclude the presence or addition of one or more other components, steps, operations and/or elements.

Unless otherwise defined, all terms (including technical and scientific terms) used herein can be used as is customary in the art to which the present invention belongs. Also, it will be further understood that terms, such as those defined in commonly used dictionaries, will not be interpreted in an idealized or overly formal sense unless expressly so defined herein.

In addition, when embodiments of the present invention are described, if it is determined that detailed descriptions of known technology related to the present invention unnecessarily obscure the subject matter of the present invention, detailed descriptions thereof will be omitted. Some terms described below are defined by considering functions in the present invention and meanings may vary depending on, for example, a user or operator's intentions or customs. Therefore, the meanings of terms should be interpreted based on the scope throughout this specification.

FIGS. 1 to 6 are schematic views for describing a method of fabricating a 3-dimensional transistor sensor according to an exemplary embodiment of the present invention.

First, referring to FIG. 1, an insulating layer 102 is formed on a silicon substrate 101. The insulating layer 102 may have a thickness of about 1 μm.

Figure 2:
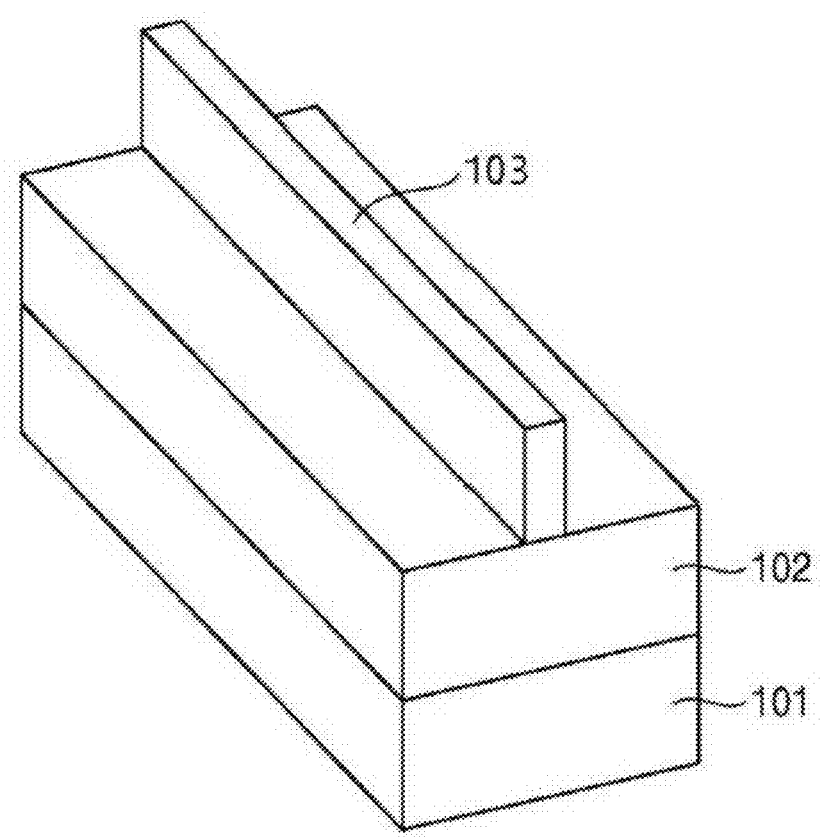

Next, referring to FIG. 2, a silicon layer is formed on the insulating layer 102. The silicon layer may have a thickness of 20 nm to 1 μm. Then, the silicon layer is etched to form a rod-type 3-dimensional silicon fin 103. The 3-dimensional silicon fin 103 may have a height ranging from 20 nm to 1 μm and a width ranging from 10 nm to 500 nm.

Figure 3:
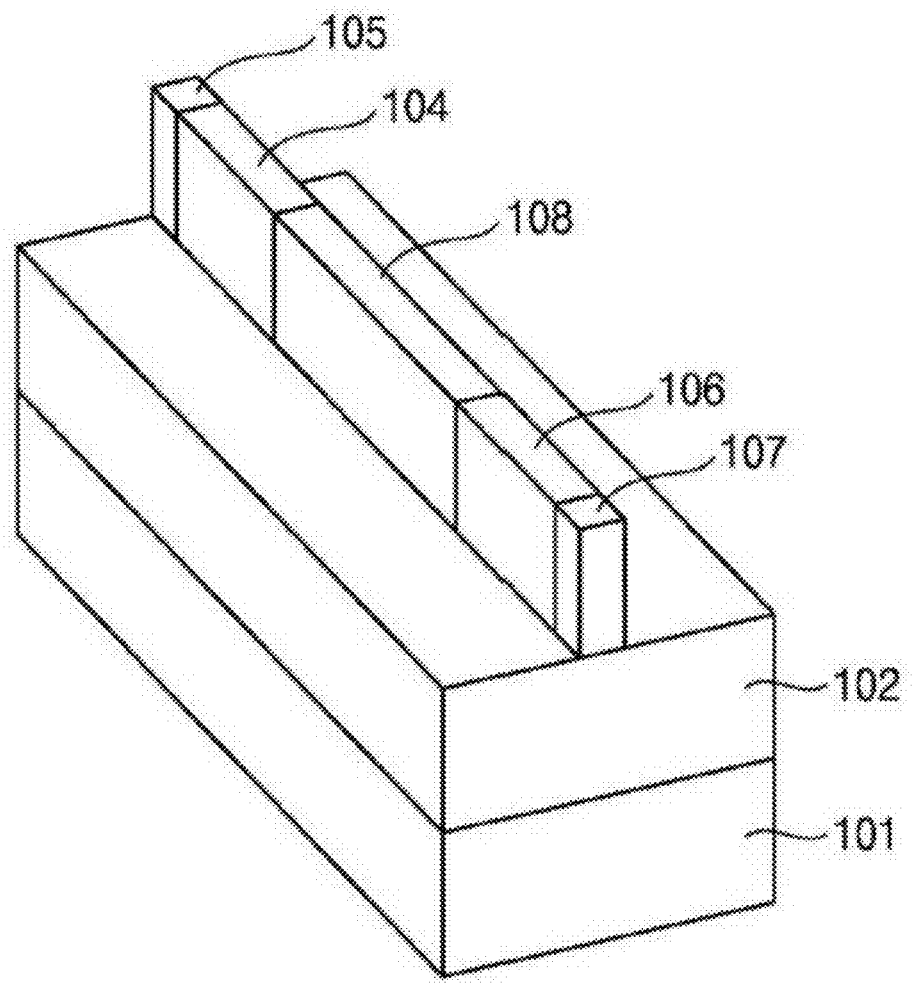

Next, referring to FIG. 3, a source area 104 and a source electrode 105 are formed at one end of the 3-dimensional silicon fin 103, and a drain area 106 and a drain electrode 107 are formed at the other end of the 3-dimensional silicon fin 103. A gate area 108 made of pure (intrinsic) silicon free of impurities may be formed at a center of the 3-dimensional silicon fin 103, P-type impurities may be implanted into the source area 104, and N-type impurities may be implanted into the drain area 106.

Figure 4:
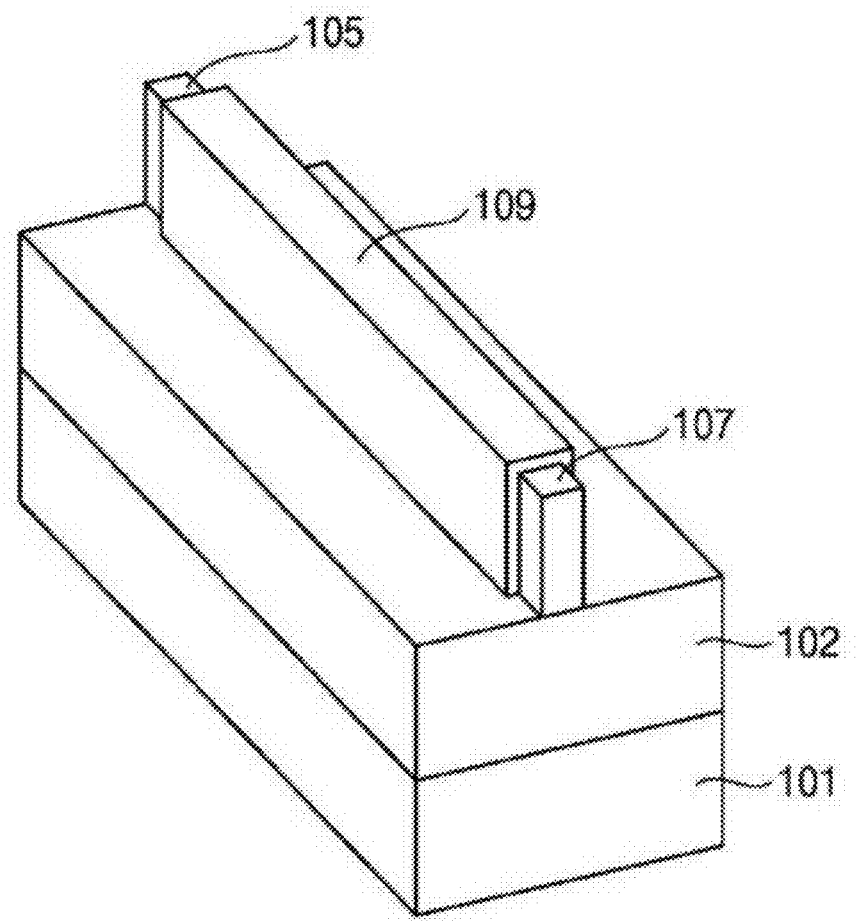

Next, referring to FIG. 4, a gate insulating layer 109 surrounds three surfaces of a gate. Accordingly, a transistor in which an impurity of source-channel-drain has a P type-intrinsic-N type form may be provided.

Figure 5:
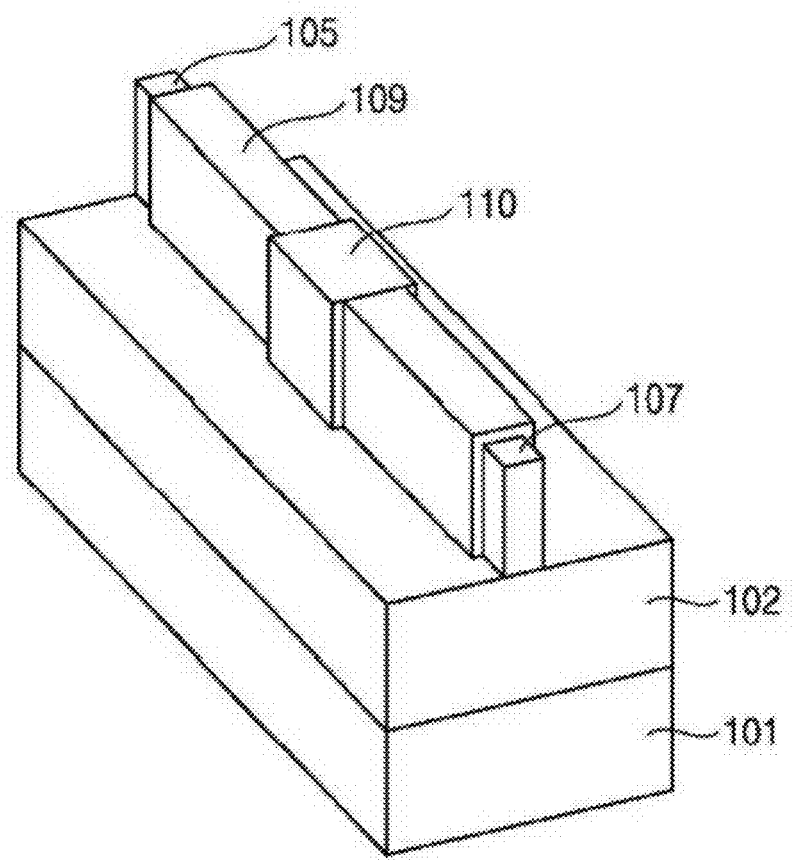
Figure 6:
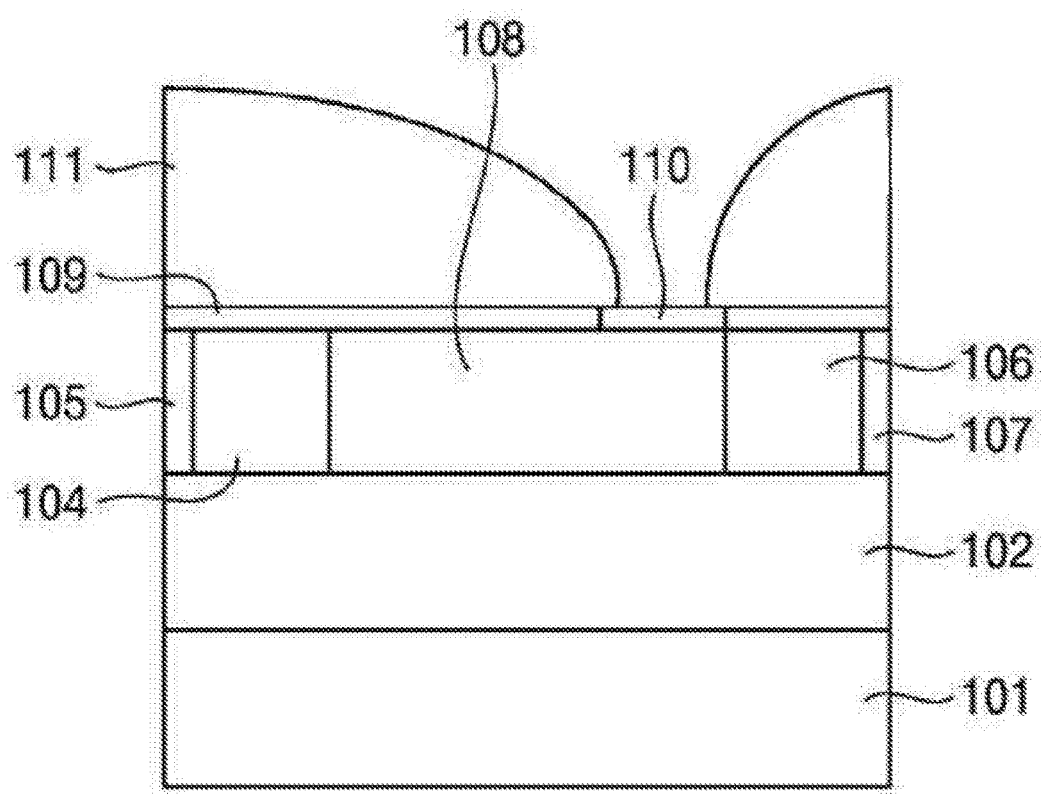
Figure 7:
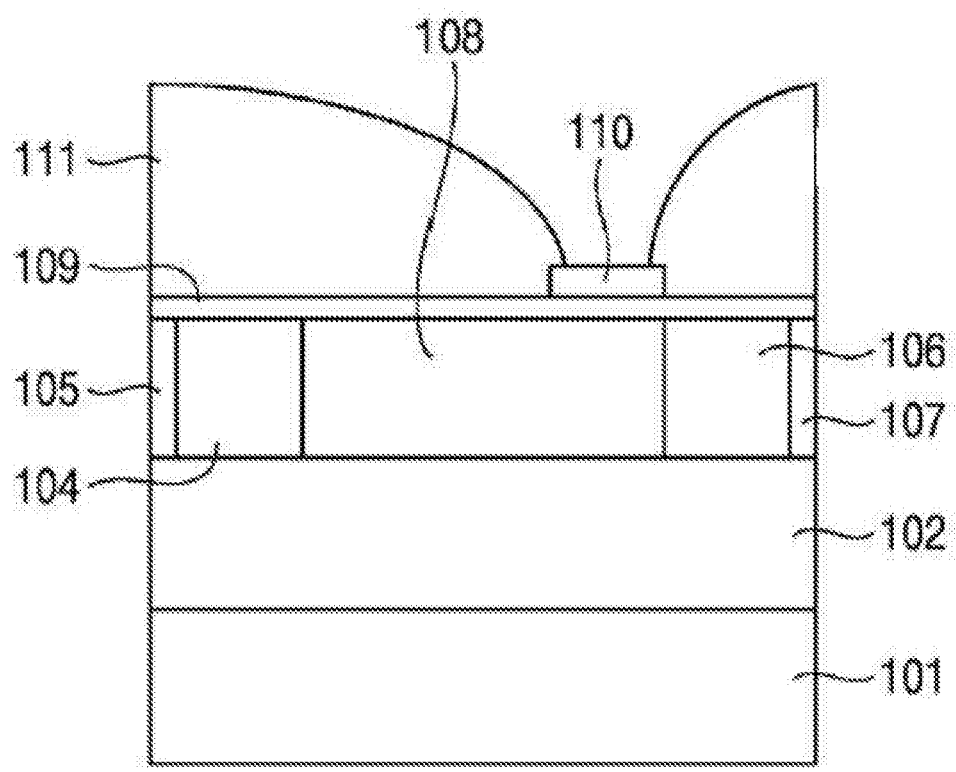

Next, referring to FIG. 5, a portion of the gate insulating layer 109, which is in contact with a drain (or a source), is removed to form a sensing gate layer 110. FIG. 6 is a cross-sectional view for describing the sensing gate layer 110. Alternatively, the gate insulating layer 109 may not be removed and a sensing gate electrode 110 may be formed on a portion of the gate insulating layer 109 as illustrated in FIG. 7.

The material for the sensing gate layer 110 may can include one any of $SiO_2$, $Si_3N_4$, $Al_2O_3$, $Pr_2O_3$, InN, $RuO_2$, RuN, $Ta_2O_5$, $SnO_2$, $V_2O_5$, $TiO_2$, $WO_3$, ZnO, $Fe_2O_3$, CuO, $Cr_2O_3$, an antibody, an enzyme, a nucleic acid (DNA), a nanomaterial, valinomicine, fluorescein, alizarin complexone, an organic conducting polymer (OCP), or the like.

For example, the antibody may include at least one of alpha-fetoprotein (AFP, an antigen of liver cancer), a prostate-specific antigen (PSA, an antigen of prostate cancer), a carcinoembryonic antigen (CEA, a cancerous antigen, which is a pan-tumor marker that is not a long-term specific tumor marker), a tissue polypeptide antigen (TPA, a tissue polypeptide antigen, which is a pan-tumor marker), a carcinoma antigen 15-3 (CA15-3, an antigen of breast cancer), and a carcinoma antigen 19-9 (CA19-9, an antigen of pancreatic cancer and biliary cancer). The enzyme may include glucose oxidase or the like. The nanomaterial may include gold nanoparticles, carbon nanotubes, graphene, graphene oxide, transition metal dichalcogenide (TMDC) two-dimensional materials, or the like.

The sensing gate or the sensing gate electrode is formed so as to surround three surfaces of the silicon fin in the corresponding sensing region, and the sensing region preferably has a length ranging from 10 nm to 500 nm.

Next, referring to FIGS. 6 and 7, an upper portion of the gate insulating layer excluding the sensing gate (or the sensing gate electrode) is sealed with epoxy (111) or the like.

The 3-dimensional transistor sensor according to the exemplary embodiment of the present invention manufactured as described above includes a transistor having a source-gate-drain on a 3-dimensional silicon fin formed on a silicon on insulator (SOI) substrate, a gate insulating layer configured to surround three surfaces of the gate, and a sensing gate layer configured to surround a portion of the gate insulating layer, which is in contact with the drain or the source.

In the 3-dimensional transistor sensor according to the exemplary embodiment of the present invention, an SOI substrate is used unlike a transistor sensor using a conventional silicon substrate, and at the same time, the SOI substrate is etched to form a 3-dimensional silicon fin. Since three surfaces of the 3-dimensional silicon fin, which are both side surfaces and an upper surface, become surfaces of the transistor, which are in contact with the gate, problems such as a leakage current, a parasitic phenomenon, an ionization phenomenon in ion collision, and the like that occur when a planar transistor is formed may be addressed.

The above-described 3-dimensional silicon fin has a structure in which a source-channel (gate area)-drain is doped with a P type-intrinsic-N type form and utilizes excellent power saving and switching performance of a field effect transistor (FET) in which a sensing gate layer is formed only in a portion of a channel area, which is in contact with a drain or a source is used. In the 3-dimensional transistor sensor according to the exemplary embodiment of the present invention, an element is configured such that a gate insulator is formed over the entire channel area, and the gate insulating layer is replaced by a sensing gate only on a portion of the source or the drain or a sensing gate electrode is formed only on the gate insulating layer of the channel or the drain side.

In the 3-dimensional transistor sensor according to the exemplary embodiment of the present invention, an off state in which no current flows is maintained in a pre-sensing state, and a sharp increase in current between the source and the drain may be caused even for a fine electric field effect through the sensing gate or the sensing gate electrode. Therefore, as compared to a conventional planar transistor sensor or finFET type sensor, the 3-dimensional transistor sensor may sense a material with improved sensitivity and at the same time, may sense with ultra-low-power at a very high speed.

Figure 8:
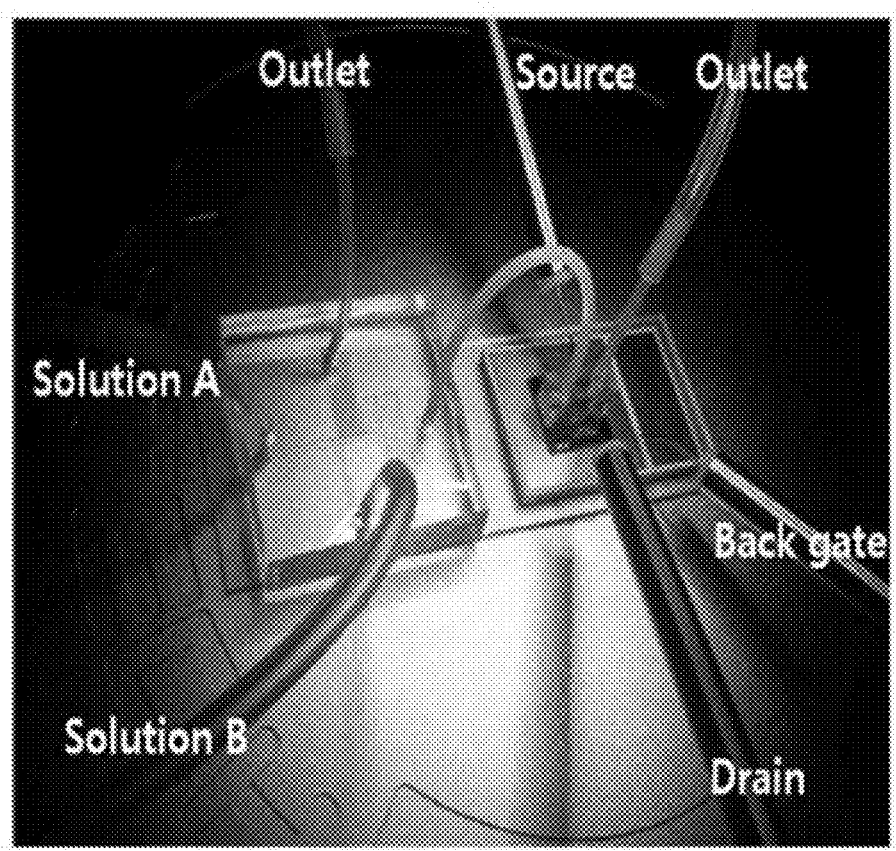
FIG. 8 is a photograph showing a test example for describing an operation principle of a 3-dimensional transistor sensor according to an exemplary embodiment of the present invention.

More particularly, an operation principle of the 3-dimensional transistor sensor according to the exemplary embodiment of the present invention will be described with reference to FIG. 8.

In the 3-dimensional transistor sensor according to the exemplary embodiment of the present invention, a sensing gate made of a material capable of sensing a material, instead of the gate insulating layer, is provided in a portion of the gate area, which is in contact with the drain (or the source), or a sensing gate electrode is provided on the gate insulating layer. In this structure, first, a sensing solution (a solution A: cAMP receptor protein (CRP)) necessary for the sensing gate is applied, and then a specific antibody of prostate cancer (a solution B: PSA) to be sensed is brought into contact with the sensing gate. Then, when a material to be sensed is adsorbed to the sensing gate electrode or is gathered around the sensing gate electrode, an electric field through the sensing gate electrode is formed due to these materials and a channel is formed under the sensing gate by the electric field. In this case, when a magnitude of a forward voltage applied between the source and the drain is large, charges may flow more easily into the channel area even with a smaller field effect, so that a large current value may be obtained by only movement of a small number of charges. Therefore, although the electric field generated by the material to be sensed is very weak, a turn-on phenomenon occurs in the transistor in which a large amount of current flows between the source and the drain. As a result, according to the 3-dimensional transistor sensor of the present invention, high sensitivity and very high speed operation are possible, and at the same time, no current flows before the transistor is turned on, and thus a sensor having ultra-low power, very high speed, and ultra-high sensitivity, without a leakage current may be provided.

Figure 9A:
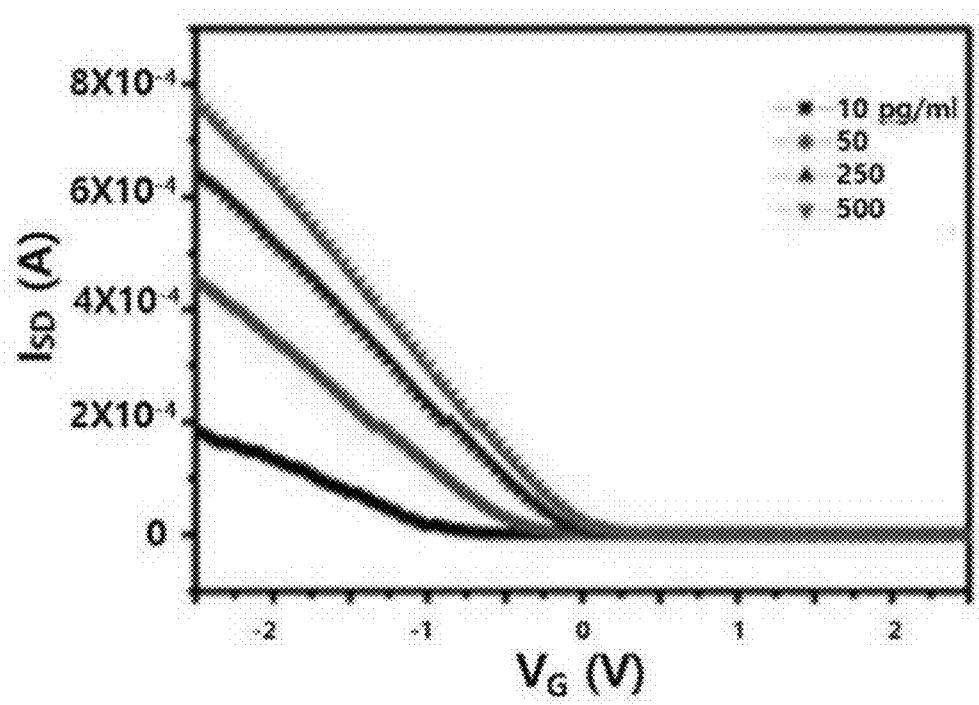
FIGS. 9A and 9B are graphs for describing operations of a 3-dimensional transistor sensor according to an exemplary embodiment of the present invention.

FIG. 9A is a graph for describing an operation of the 3-dimensional transistor sensor according to an exemplary embodiment of the present invention. Referring to FIG. 9A, a current generated in the 3-dimensional transistor sensor is measured according to a concentration of a PSA when a voltage of 0.0, 0.6, 1.5, or 2.0 V is applied to the sensing gate or the sensing gate electrode. From the experimental results, it can be seen that no current flows when the gate voltage is 0, and a concentration of the sensed material is very low as the gate voltage increases, and, even though the electric field thus formed is very weak, the transistor sensor turns on and a linearly increasing current may be obtained.

Figure 9B:
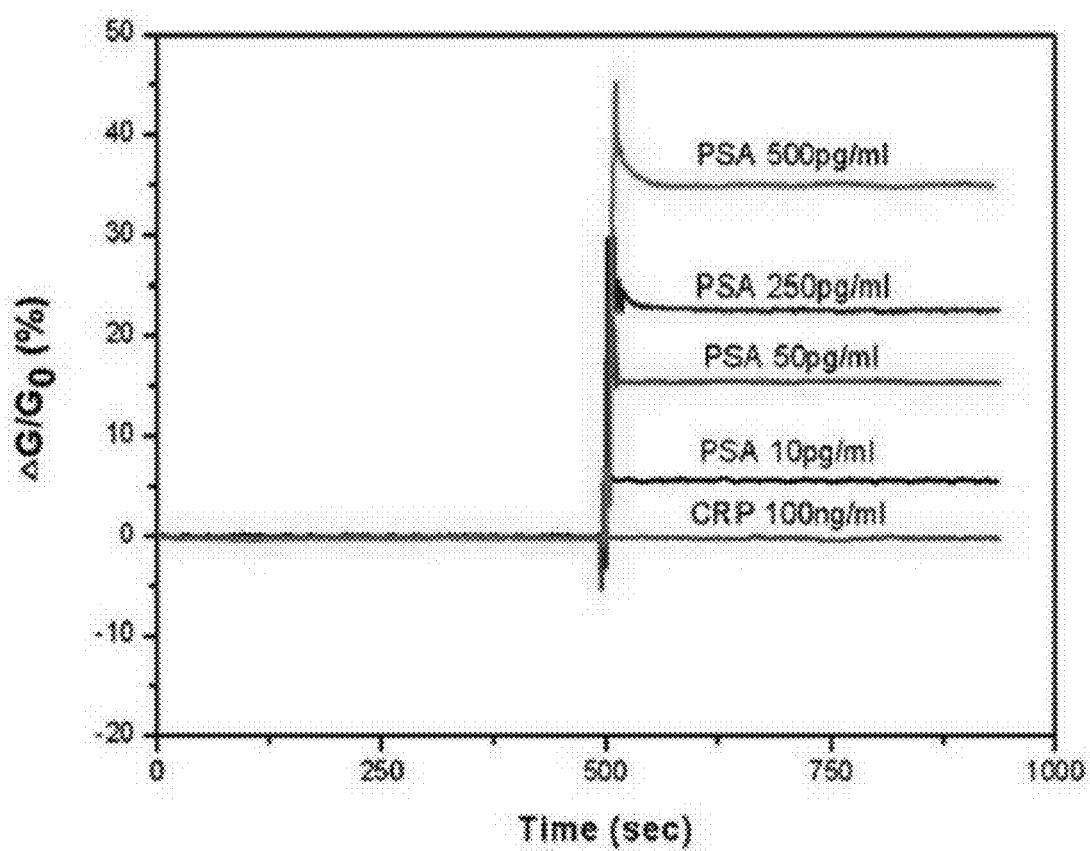

In addition, FIG. 9B is a graph showing changes of sensitivity of the sensor according to a change of a concentration of a PSA after 100 ng/ml of a CRP is brought into contact with the sensing gate. Referring to FIG. 9B, it can be seen that a response speed of the 3-dimensional transistor sensor is very fast according to the concentration of the PSA. As a result of measuring continuously changing the concentration of PSA, it is shown that the 3-dimensional transistor sensor responds immediately within 100 nsec and sensitivity increases as the concentration of the PSA increases. Therefore, when using the 3-dimensional transistor sensor, high sensitivity and very high speed operation may be achieved and no current flows before the transistor is turned on, and thus an ultra-low power, very high speed, and high sensitivity sensor which does not have a leakage current may be provided.

Figure 10:
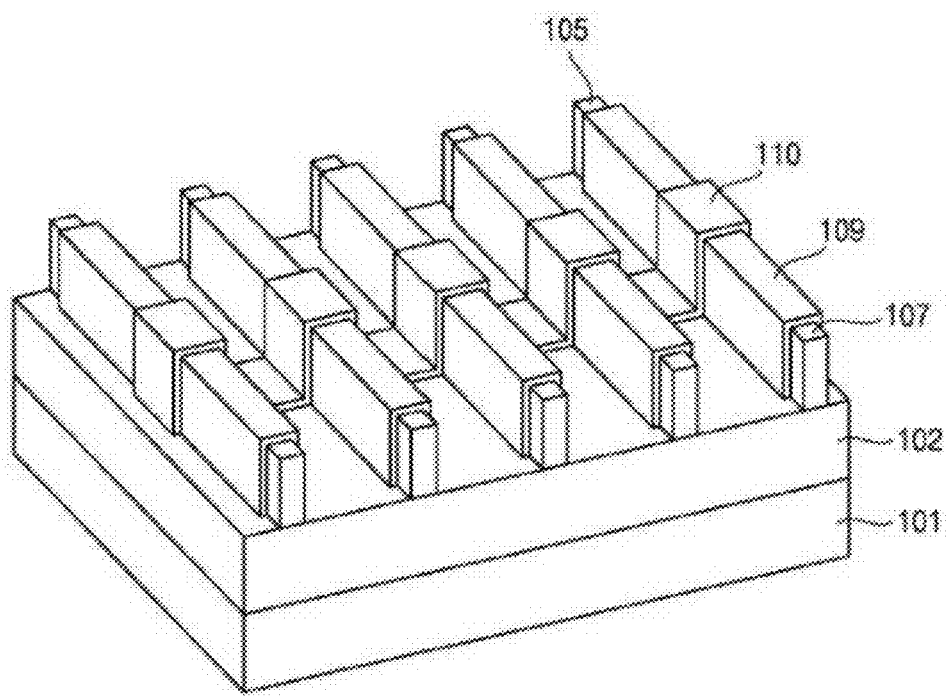
FIG. 10 is a 3-dimensional view for describing a 3-dimensional transistor sensor array according to an exemplary embodiment of the present invention.

FIG. 10 is a 3-dimensional view for describing a 3-dimensional transistor sensor array according to an exemplary embodiment of the present invention. Referring to FIG. 10, an example in which 3-dimensional silicon fins are arranged in an array form on an SOI substrate, and a sensing gate electrode 110 is formed on a gate insulating layer of each of the silicon fins is illustrated.

As described above, according to the present invention, as compared to a conventional transistor sensor using an external power saving circuit, a low power operation can be performed in a semiconductor sensor itself and ultra-low power driving is possible, and a target material can be sensed with high sensitivity.

In addition, as compared to a conventional low-power sensor using a semiconductor nanomaterial, existing silicon-based technology can be utilized because etching-deposition-doping process technology currently used in industry can be applied to a sensor as it is and the sensor is manufactured based on silicon.

Although the embodiments of the 3-dimensional transistor sensor according to the present invention have been described above, the present invention is not limited thereto, but may be variously modified and embodied within the scope of the claims, detailed description and accompanying drawings, and this also belongs to the present invention.

What is claimed is:

1. A method of fabricating a 3-dimensional transistor sensor, the method comprising:
   forming an insulating layer on a silicon substrate;
   forming a silicon layer on the insulating layer; and
   forming a 3-dimensional (3D) silicon fin by removing a part of the silicon layer from the silicon layer by etching;
   forming a source area and a source electrode at one end of the 3D silicon fin, the source area being formed next to the source electrode by implanting a first impurity into the 3D silicon fin, forming a drain area and a drain electrode at the other end the 3D silicon fin, the drain area being formed next to the drain electrode by implanting a second impurity into the 3D silicon fin, and forming a gate area at a center portion of the 3D silicon fin;
   forming a gate insulating layer over the 3D silicon fin such that the gate insulating layer surrounds three surfaces of the gate area;
   forming a sensing gate layer configured to sense a material; and
   sealing an upper portion of the gate insulating layer excluding the sensing gate layer,
   wherein the sensing gate layer is formed by removing a portion of the gate insulating layer, which is in contact with the drain area or the source area.

2. The method of claim 1, wherein the 3D silicon fin has a height of 20 nm to 1 μm and a width of 10 nm to 500 nm.

3. The method of claim 1, wherein the first impurity is a P-type impurity, and the second impurity is an N-type impurity.

4. The method of claim 1, wherein the sensing gate layer is formed as a sensing gate electrode on a portion of the gate insulating layer.

5. The method of claim 1, wherein the sensing gate layer material is made of any one of $SiO_2$, $Si_3N_4$, $Al_2O_3$, $Pr_2O_3$, InN, $RuO_2$, RuN, $Ta_2O_5$, $SnO_2$, $V_2O_5$, $TiO_2$, WOE, ZnO, $Fe_2O_3$, CuO, $Cr_2O_3$, an antibody, an enzyme, a nucleic acid (DNA), a nanomaterial, valinomicine, fluorescein, alizarin complexone, and an organic conducting polymer (OCP).

6. The method of claim 1, wherein the sensing gate layer has a length of 10 nm to 500 nm.

7. A 3-dimensional transistor sensor comprising:
   an insulating layer formed on a silicon substrate;
   a 3-dimensional (3D) silicon fin formed on the insulating layer such that the insulating layer is interposed between the 3D silicon fin and the silicon substrate, wherein the 3D silicon fin includes
   a gate disposed at a center portion of the 3D silicon fin,
   a source disposed at one side of the gate in the 3D silicon fin, and
   a drain disposed at the other side of the gate in the 3D silicon fin;
   a gate insulating layer formed over the 3D silicon fin such that the gate insulating layer surrounds three surfaces of the gate; and
   a sensing gate layer configured to surround a portion of the gate insulating layer and formed by removing a portion of the gate insulating layer, which is in contact with the drain or the source,
   wherein, when a material is sensed by the sensing gate layer, a current flows between the source and the drain.

8. A 3-dimensional transistor sensor comprising:
   an insulating layer formed on a silicon substrate;
   a 3-dimensional (3D) silicon fin formed on the insulating layer such that the insulating layer is interposed between the 3D silicon fin and the silicon substrate, wherein the 3D silicon fin includes
   a gate disposed at a center portion of the 3D silicon fin,
   a source disposed at one side of the gate in the 3D silicon fin, and
   a drain disposed at the other side of the gate in the 3D silicon fin;
   a gate insulating layer formed over the 3D silicon fin such that the gate insulating layer surrounds three surfaces of the gate; and
   a sensing gate electrode formed on the gate insulating layer to surround a portion of the gate in contact with the drain or the source,
   wherein, when a material is sensed by the sensing gate electrode, an electric field through the sensing gate electrode is formed due to the material whereby a current flows between the source and the drain, and when no voltage is applied to the sensing gate electrode, an off state in which no current flows between the source and the drain is maintained.

9. The 3-dimensional transistor sensor of claim 7, wherein, when no voltage is applied to the sensing gate layer, an off state in which no current flows between the source and the drain is maintained, and when a material is sensed by the sensing gate layer, an electric field through the sensing gate layer is formed due to the material.

10. The 3-dimensional transistor sensor of claim 7, wherein the sensing gate layer material includes any one of $SiO_2$, $Si_3N_4$, $Al_2O_3$, $Pr_2O_3$, InN, $RuO_2$, RuN, $Ta_2O_5$, $SnO_2$, $V_2O_5$, $TiO_2$, $WO_3$, ZnO, $Fe_2O_3$, CuO, $Cr_2O_3$, an antibody, an enzyme, a nucleic acid (DNA), a nanomaterial, valinomicine, fluorescein, alizarin complexone, and an organic conducting polymer (OCP).

11. A 3-dimensional transistor sensor array in which the 3-dimensional transistor sensors according to claim 7 are arranged in an array form.

12. The 3-dimensional transistor sensor of claim 8, wherein the sensing gate electrode material includes any one of $SiO_2$, $Si_3N_4$, $Al_2O_3$, $Pr_2O_3$, InN, $RuO_2$, RuN, $Ta_2O_5$, $SnO_2$, $V_2O_5$, $TiO_2$, $WO_3$, ZnO, $Fe_2O_3$, CuO, $Cr_{203}$, an antibody, an enzyme, a nucleic acid (DNA), a nanomaterial, valinomicine, fluorescein, alizarin complexone, and an organic conducting polymer (OCP).

13. A 3-dimensional transistor sensor array in which the 3-dimensional transistor sensors according to claim 8 are arranged in an array form.

\* \* \* \* \*